US011759363B2

(12) United States Patent
Xiao

(10) Patent No.: US 11,759,363 B2
(45) Date of Patent: Sep. 19, 2023

(54) WIPER SYSTEM

(71) Applicant: Shenzhen Ruikeda Silicone Mold Products Co., Ltd, Guangdong (CN)

(72) Inventor: Wenzi Xiao, Shenzhen (CN)

(73) Assignee: Shenzhen Ruikeda Silicone Mold Products Co., LTD, Guangdong (CN)

( * ) Notice: Subject to any disclaimer, the term of this patent is extended or adjusted under 35 U.S.C. 154(b) by 180 days.

(21) Appl. No.: 17/395,376

(22) Filed: Aug. 5, 2021

(65) Prior Publication Data
US 2023/0043961 A1    Feb. 9, 2023

(51) Int. Cl.
*A61F 9/02* (2006.01)
*A63B 33/00* (2006.01)
*G02C 11/08* (2006.01)

(52) U.S. Cl.
CPC ............ *A61F 9/029* (2013.01); *A63B 33/002* (2013.01); *G02C 11/08* (2013.01)

(58) Field of Classification Search
CPC ......... A42B 3/26; A61F 9/029; A63B 33/002; B60S 1/14; B60S 1/16; B60S 1/26; B63C 11/12
USPC ............... 15/250.3, 250.001, 250.27, 250.15
See application file for complete search history.

(56) References Cited

U.S. PATENT DOCUMENTS

| | | | |
|---|---|---|---|
| 1,448,003 A * | 3/1923 | Richards | B60S 1/14 |
| | | | 15/250.24 |
| 1,509,699 A * | 9/1924 | Atchison | B60S 1/16 |
| | | | 310/83 |
| 1,618,068 A * | 2/1927 | Dayton | B60S 1/14 |
| | | | 15/250.3 |
| 1,839,175 A | 12/1931 | Hueber | |
| 2,253,538 A | 8/1941 | Sirch | |
| 2,721,352 A | 10/1955 | Oishei | |
| 2,888,703 A | 6/1959 | Karwowska | |
| 3,754,298 A | 8/1973 | Menil | |
| 3,890,647 A | 6/1975 | Warncke | |
| 4,027,354 A * | 6/1977 | Burpee | A42B 3/26 |
| | | | 74/25 |
| 4,215,437 A * | 8/1980 | Kao | A42B 3/26 |
| | | | 2/5 |
| 4,353,134 A | 10/1982 | Macnabb | |
| 4,789,233 A | 12/1988 | Arsenault et al. | |
| 6,640,379 B1 | 11/2003 | Scribner | |
| 6,722,766 B1 | 4/2004 | Myette | |
| 7,181,778 B1 * | 2/2007 | Garraffa | B63C 11/12 |
| | | | 2/427 |
| 8,209,783 B1 | 7/2012 | Eagle | |
| 9,220,930 B2 * | 12/2015 | Robey | A62B 18/02 |
| 10,426,665 B1 * | 10/2019 | Fridie | A61F 9/02 |
| 2007/0283485 A1 * | 12/2007 | Tseng | A42B 3/26 |
| | | | 15/250.31 |

(Continued)

FOREIGN PATENT DOCUMENTS

CN    203763793 U    8/2014
CN    203965754 U    11/2014

(Continued)

*Primary Examiner* — F Griffin Hall
(74) *Attorney, Agent, or Firm* — Jeffrey G. Degenfelder; Carstens, Allen & Gourley, LLP

(57) ABSTRACT

The vision protection apparatus of the present invention includes a wiper mechanism which allows a user to clear condensation from an inner surface of a lens without removing the vision protection apparatus.

20 Claims, 7 Drawing Sheets

(56) References Cited

U.S. PATENT DOCUMENTS

2008/0184464 A1\* 8/2008 Chen .................. A42B 3/26
                                                           2/427
2016/0327810 A1\* 11/2016 Cross .................. B63C 11/12

FOREIGN PATENT DOCUMENTS

| CN | 212522169 U    |   | 2/2021 |              |
|----|----------------|---|--------|--------------|
| DE |    575868 C    | \* | 4/1933 |              |
| DE |   2105753 A1   | \* | 8/1971 |              |
| FR |   2245971 A1   | \* | 4/1975 |              |
| GB |   2177290 A    | \* | 1/1987 | ........ G02C 11/08 |
| GB |   2177290 A    |   | 1/1987 |              |

\* cited by examiner

WIPER SYSTEM

BACKGROUND OF THE INVENTION

1. Technical Field of the Invention

The present invention is generally directed to a system for maintaining clear visibility for interior lens surfaces of various vision protective devices. More specifically, the present invention is directed to a mechanism fitted to an underwater swimming mask, ski or safety goggles having a lens with an inner surface, a frame mounting the lens in spaced relationship to a user's eyes and a face-fitting skirt peripherally extending from the frame. The improvement comprises a wiper mechanism mounted therein that, when actuated, generates a sweeping movement across a viewing area of each lens, in wiping contact with the lens inner surface so as to dissipate condensation collected on the lens inner surface and to clear the viewing area of the lens.

2. Description of the Related Art

Most conventional devices having vision protective lenses like safety goggles, face shields, or other eye/face protective wear are provided without measures for removing condensation, which typically forms on the interior surface of the lenses. Moisture typically forms on interior surfaces due to a temperature difference between the inner and outer surface of the lens that causes moisture in the air to condense on the inner lens surface. For example, swimmers engaged in diving activities typically wear diving goggles to protect their eyes. However, the water temperature outside the google lens is oftentimes lower when compared with the air temperature inside the goggles, causing a fogging condensation to form on the inner surface of the lens obscuring the swimmer's vision.

A user is typically expected to remove the protective lenses or goggles and manually wipe or rinse off the condensation before proceeding to put the protective eye wear back on. For example, with diving goggles a user typically pulls the googles away from the user's face to break the seal of the goggle's skirt allowing water to flood the goggle interior lens before evacuating the water from the goggle mask by blowing air through the nose and resealing the skirt to the wearer's face. While this is somewhat adequate for snorkeling operations, at greater depths it becomes increasingly hazardous and unmanageable.

A variety of proposals have previously been made to mitigate the fogging of such inner lens surfaces. For example, antifog sprays which coat the inner lens surface have been used with varied success. U.S. Pat. No. 4,353,134 discloses a pair of swim goggles having a wiper means mounted on the interior of the lens that is gravity-actuated by the swimmer rotating his head from side to side. While somewhat effective, they are far from optimal and only work if and when the swimmer rotates his head. A need, therefore, exists for an improved and more simplified mechanism for wiping away condensation from the inside of a protective lens that a user can quickly and effectively actuate without moving his head from side to side.

SUMMARY OF THE INVENTION

The present invention relates to an improvement in diving masks, ski or safety goggles and/or other vision protective devices that enables the wearer to remove condensation moisture from the interior surface of lenses without having to remove the vision protective device. The present invention provides a wiper mechanism, a method of manufacturing a wiper mechanism, and a vision protection apparatus. The mechanisms employed by the present invention will accomplish this in a cost effective and efficient manner.

In at least one example, the wiper mechanism includes a transmission housing, a plunger device with a biasing element, and two wiper arms. The plunger device comprises gear teeth and is slideably coupled to the housing. The biasing element is positioned between the transmission housing and the plunger device. The two wiper arms are pivotally connected to the transmission housing. Each wiper arm comprises a first and a second end. The wiper arm pivot gear comprises gear teeth and is positioned at the first or proximal end of each wiper arm. Each wiper arm further includes a wiper blade element that is pivotally attached to the second or distal end of the wiper arm. The two wiper arm pivot gear teeth mesh with the plunger device gear teeth. When a user depresses the plunger device, the two wiper arms pivot upwardly. When the user subsequently releases the plunger device, the biasing element forces the plunger device to extend, which causes the two wiper to pivot downwardly.

In at least one example, the method of manufacturing a wiper mechanism comprises providing a transmission housing. Forming a plunger device, comprising gear teeth, for slidably coupling to the transmission housing. Forming two wiper arms that are pivotally connected to the transmission bracket. Each wiper arm comprises a first and a second end. Each wiper arm also has a pivot gear positioned at the first end of the wiper arm. Moreover, each wiper arm has a wiper blade element positioned at the second end of the wiper arm. Providing a biasing element for positioning between the transmission bracket and the plunger device.

In at least one example, the vision protection apparatus contains, at least one lens, a frame, a means for attaching the frame to the head of a user, and a wiper mechanism. The frame secures the at least one lens. The wiper mechanism contains a transmission bracket housing, a plunger device, a biasing element, and two wiper arms. The transmission bracket contains an alignment hole. The plunger device contains gear teeth. The plunger device is fitted in the alignment hole such that the plunger device slides within the transmission bracket housing. The biasing element is positioned between the transmission bracket housing and the plunger device. Finally, each of the wiper arms contains a pivot gear and a wiping means. The wiper arm pivot gear contains gear teeth. Each wiper arm is pivotally connected to the transmission bracket housing and each wiper arm's pivot gear teeth meshes with the plunger device gear teeth. The wiping means pivots across the at least one lens when the plunger device is depressed and when it is released.

BRIEF DESCRIPTION OF THE DRAWINGS

A more complete understanding of the method and apparatus of the present invention may be had by reference to the following detailed description when taken in conjunction with the accompanying drawings, wherein:

FIG. 3b is a close-up view of the example of the wiper mechanism of the present invention shown in FIG. 3a;

FIG. 5 is a detailed view of the wiper mechanism shown in FIG. 4a.

Figure 1:
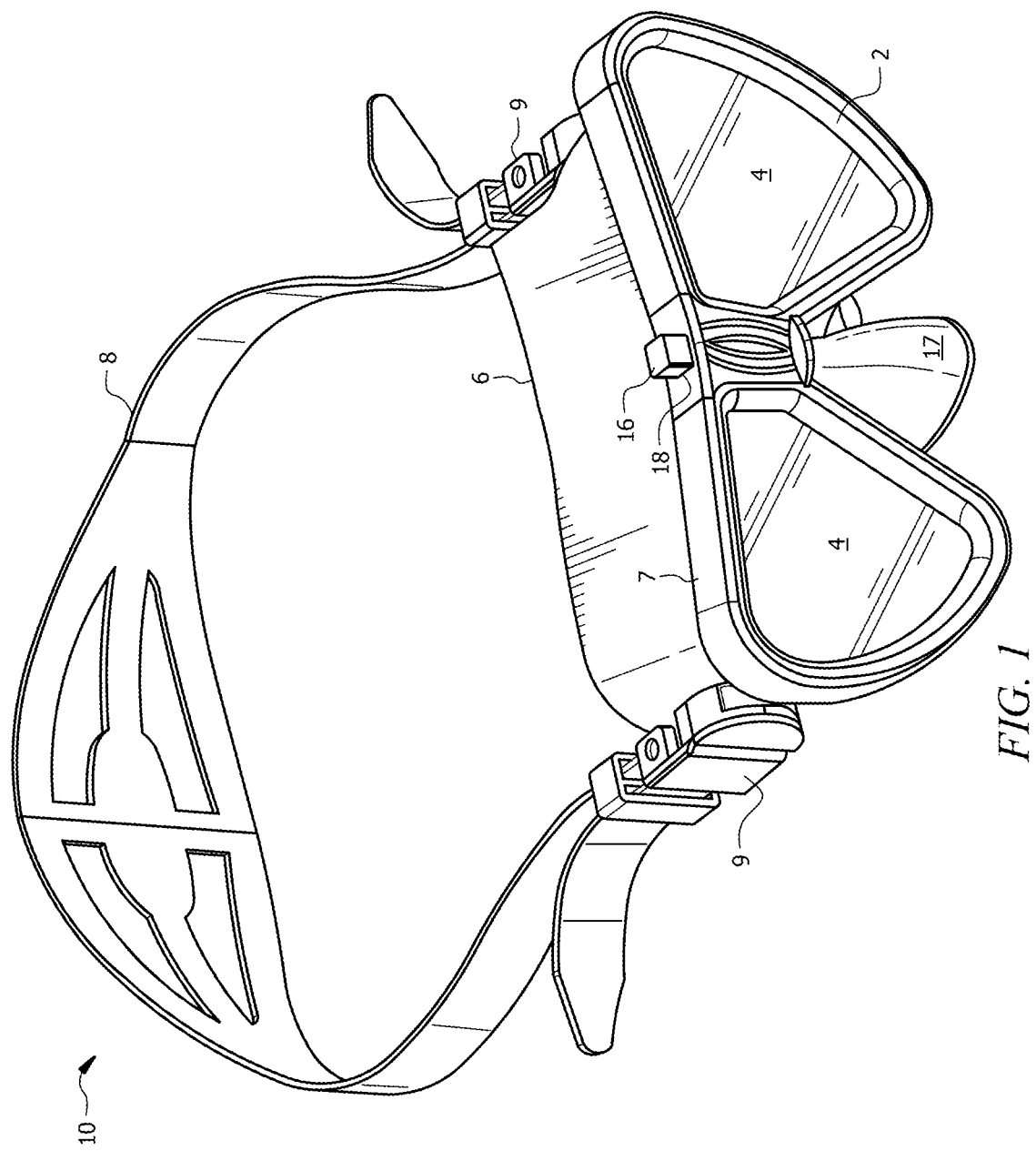
FIG. 1 is a perspective view of one example of the present invention as integrated into a diving goggle.
Figure 2:
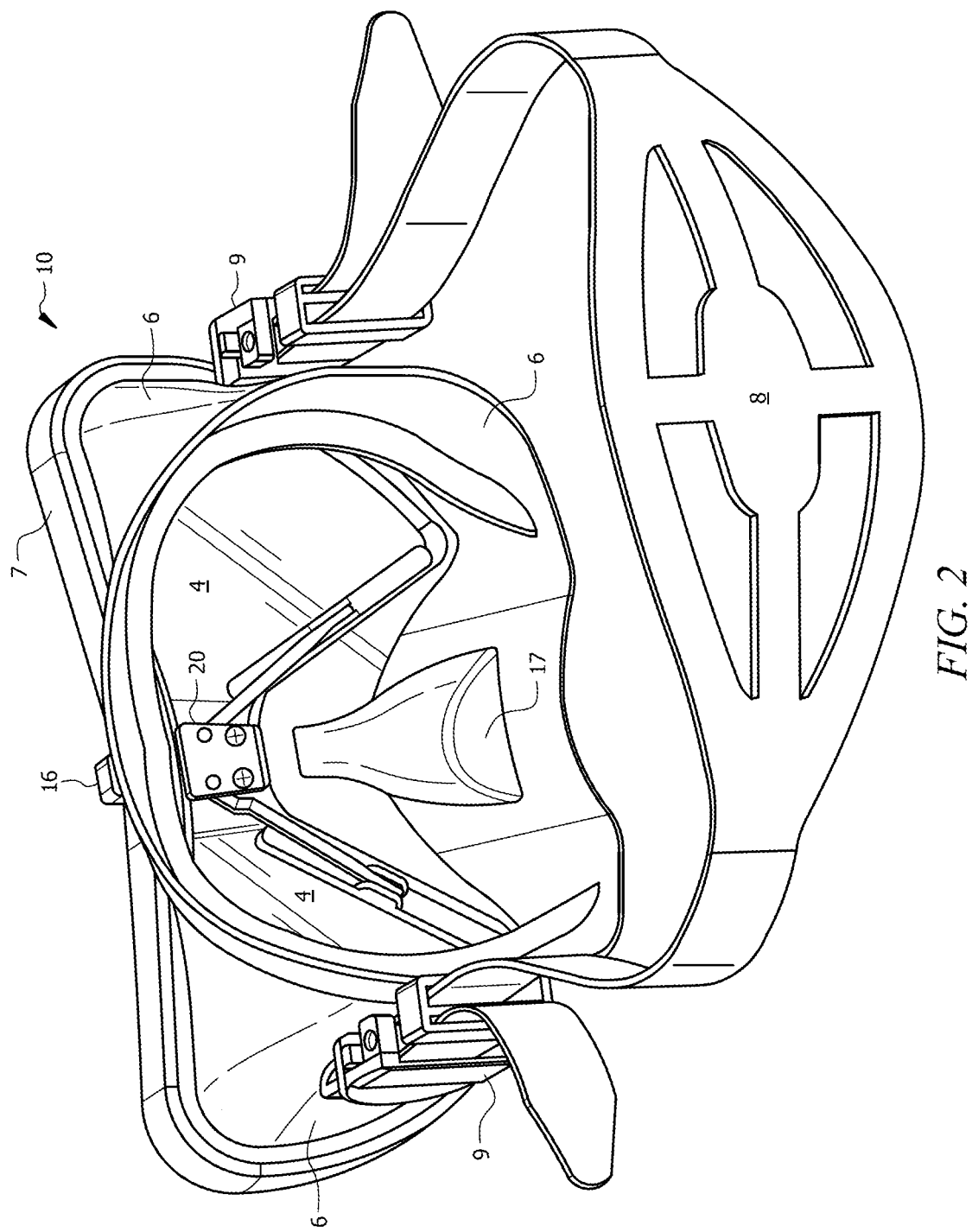
FIG. 2 is a rear perspective view thereof.

Where used in the various figures of the drawing, the same numerals designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

All figures are drawn for ease of explanation of the basic teachings of the present invention only; the extensions of the figures with respect to number, position, relationship, and dimensions of the parts to form the preferred example will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

DETAILED DESCRIPTION OF THE INVENTION

The wiper mechanism of the present invention may be incorporated into a wide variety of goggles, face shields, or other eye/face protective wear. For example, FIG. 1 depicts an example of a diving mask 10 featuring an embodiment of the wiper mechanism 20 of the present invention. With reference now to the Figures, and in particular, FIGS. 1-4A, and 5, the mask 10 may include at least one lens 4 mounted in a frame 7 using a lens holder 2 for each lens 4. The frame 7 for mounting the lens 4 is in a spaced relationship to a swimmer's eye, and attached to a water-excluding face-fitting skirt 6 peripherally extending from the frame 7. Furthermore, this mask skirt 6 may form a waterproof seal around the face of a user. While the preferred example shown in the Figures comprises a waterproof mask skirt 6, it is understood that the mask skirt could only provide partial covering or be absent entirely. The mask 10 may also include a head strap 8 affixed to strap adjusters 9, which in turn are affixed to the mask skirt 6 or, alternatively, the frame 7. A nose section of mask skirt 17 extends from the front of the mask skirt 6 to an area beneath the frame 7.

In the embodiment of the mask 10 depicted in the Figures, the central top section of the frame 7 includes an aperture 18 through which a plunger device 40 of the wiper mechanism 20 extends. The mask 10 may further include a waterproof cover 16 over the plunger device to prevent water from leaking through the aperture 18 into the inside of the mask 10. Alternatively, or in addition, the plunger device 40 may include an O-ring device that seals the aperture 18.

Figure 3A:
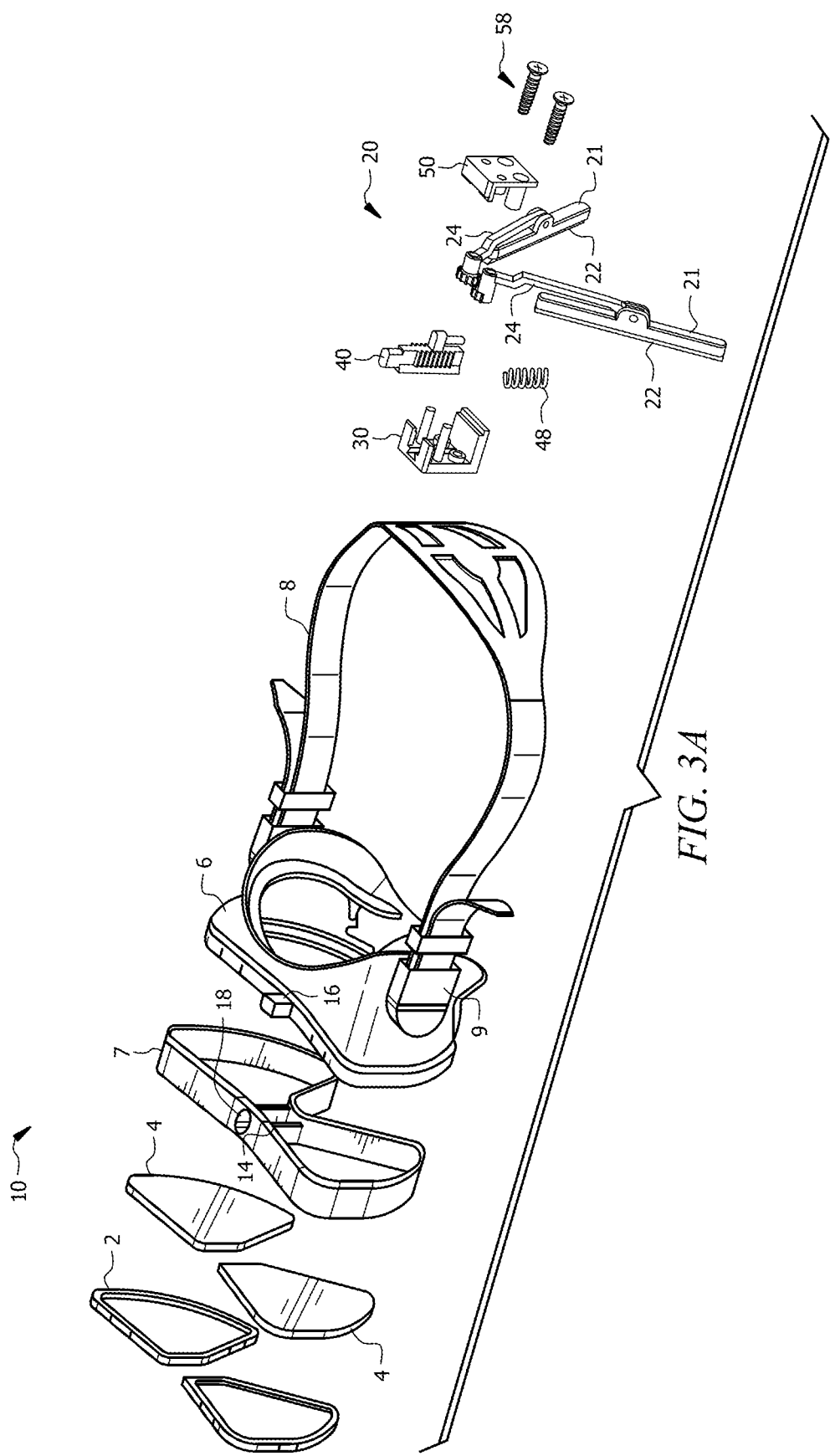
FIG. 3a is an exploded rear perspective view thereof.

Turning to FIG. 3A, an exploded rear perspective of one example of the invention as integrated into a diving goggle, the components of the mask 10 and the wiper mechanism 20 appear. The wiper mechanism 20 is fitted into a recess 14 (FIG. 5) formed in the frame 7. As depicted in the drawings, the recess 14 is located directly below and accessible from the aperture 18 formed into the frame 7.

Figure 3B:
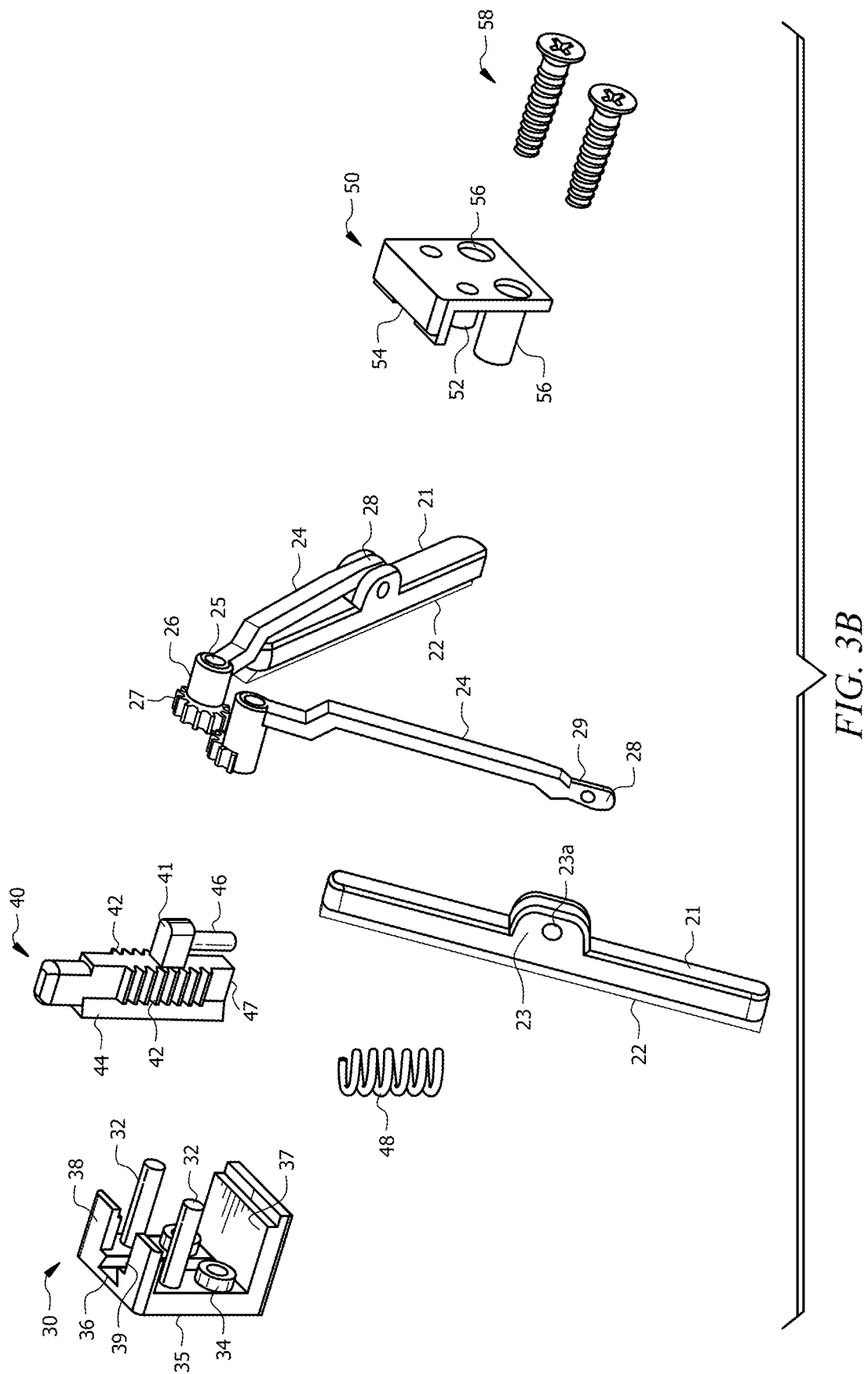

As shown in FIGS. 3A-B, in one example, the components of the wiper mechanism 20 include a housing comprising a transmission bracket 30 and cover 50, a plunger device 40 with a biasing element 48, and two wiper arm assemblies, each including a wiper arm 24 and its respective wiper blade element 21. In the depicted embodiment, the wiper mechanism 20 may further include two fixing screws 58 for attaching the transmission bracket cover 50 to the transmission bracket 30. In addition, the fixing screws 58 may also be used to fixably attach the wiper mechanism 20 into the recess 14 formed in the frame 7 of the mask 10. Alternatively, the wiper mechanism 20 may be attached to the recess 14 formed in the frame 7 by friction fit or adhesive bonding.

As depicted in the Figures, the transmission bracket 30 comprises a top surface 38, a bottom surface 37, and a vertical wall 35. In at least one example, two upper aligner posts 32 extend perpendicularly from the vertical wall 35. As will be demonstrated shortly, the upper aligner posts 32 each act as pivot points for their respective wiper arms 24. In at least one example, two lower alignment tubes 34 also extend perpendicularly from the vertical wall 35 for receiving fixing screws 58. The transmission bracket 30 further includes a top alignment hole 39 formed through the top surface 38 of the transmission bracket 30 and includes an alignment slot 36 formed into the transmission bracket vertical wall 35. The alignment hole 39 and slot 36 are designed to slidably receive a plunger device 40 and prevent racking of the plunger device 40 during operation. The alignment slot 36 preferably includes a cross-section that is complementary in shape to an aligner surface 44 formed on the plunger device 40.

In a preferred example the plunger device 40 comprises gear teeth. As depicted in the Figures, in at least one example, the gear teeth are integrated into opposing vertical gear racks 42. The plunger device 40 further comprises a vertical stop post 46. The vertical stop post 46 extends away in a parallel configuration to the plunger device 40. In one embodiment, the vertical stop post 46 is designed to receive a biasing device 48 such as a spring. The plunger device 40 is configured to slidably couple with the transmission bracket 30. In yet other examples, the plunger device 40 may further comprise an aligner surface 44. The aligner surface 44 is configured to slidably couple within the alignment slot 36, such that the plunger device 40 may vertically slide within the transmission bracket 30.

With reference again to FIG. 3B, in the depicted embodiment the wiper arm assemblies each include a wiper arm 24 and its respective wiper blade element 21. Each wiper arm 24 contain a wiper arm pivot gear 26, comprising gear teeth 27, positioned at a first or proximal end of the wiper arm 24 and a wiper blade element 21 positioned at a second or distal end 28 of the wiper arm 24. In a preferred example each wiper arm 24 comprises a pivot point aperture 25 on a first or proximal end, wherein each wiper arm's pivot point aperture 25 is pivotally connected to one of the upper aligner post 32 that extend perpendicularly from the vertical wall 35. The first or proximal end of each wiper arm 24 further includes a pivot gear 26. In the depicted embodiment, the pivot gear 26 includes a set of gear teeth 27 designed to intermesh with gear teeth on the plunger device 40.

The second or distal end 28 of each wiper arm 24 includes a pivot point 29 connected to a wiper blade coupler bracket 23 on the wiper blade element 21. The wiper blade coupler bracket 23 may affix a wiper blade 22. For example, in one embodiment the pivot point 29 may comprise a fixed pin extending from the wiper arm 24 and configured to clip onto the wiper blade pivot point 23a on the wiper blade coupler bracket 23. In another embodiment, the pivot point 29 may comprise a hole formed in the second or distal end 28 of the wiper arm 24, wherein a separate pivot pin (not shown) is inserted and used to couple the pivot point 29 with the wiper blade pivot point 23a on the wiper blade coupler bracket 23.

In the depicted embodiment, the transmission bracket cover 50 secures the plunger device 40 and the two wiper arms 24 within the transmission bracket 30. In an example, the transmission bracket cover may comprise two alignment collars 52, two fixing and alignment tubes 56, and a longitudinal stop surface 54. The two alignment collars 52 may be affixed to the transmission bracket cover 50 and may be configured to couple with the two upper aligner post/pivot points 32 on the transmission bracket 30. The two fixing and alignment tubes 56 may also be affixed to the transmission bracket cover 50 and may be configured to couple with the two lower alignment tubes 34 on the transmission bracket 30. The transmission bracket cover may be secured to the transmission bracket 30 by a securing mechanism 58. For example, in one embodiment the securing mechanism 58 include two fixing screws which couple with the two fixing and alignment tubes 56 and the lower alignment tubes 34, but this is only an example and other securing mechanism may be used.

Figure 4A:
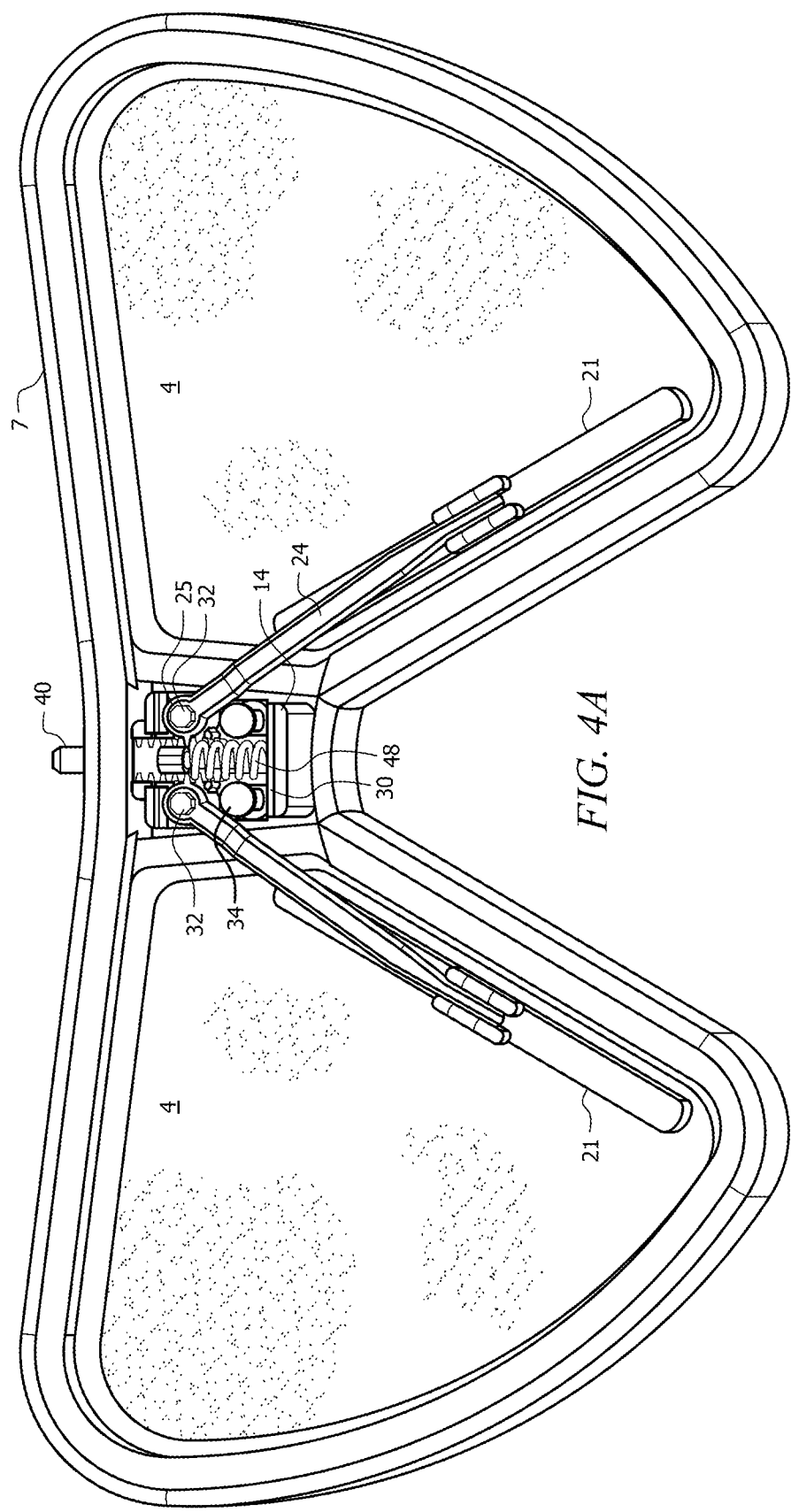
FIGS. 4a and b are rear elevation views of the goggle lens shown in FIG. 3a depicting the movement of the wiper mechanism.

With reference now to FIG. 4A an example of the wiper mechanism 20 fitted to the frame 7 of a diving mask 10 is depicted. In this example, the transmission bracket 30 of the housing is configured into a recess 14 formed in frame 7. The plunger device 40 is slidably coupled to the transmission bracket 30 and extends outwardly past the alignment hole 39 and through the aperture 18 formed in the top of frame 7. The biasing element 48 is configured about the vertical stop post 46 and causes the bottom 47 of the plunger device 40 to position above the transmission bracket bottom surface 37 when not activated (i.e., depressed). Similarly, the top 41 of the vertical stop post 46 may limit the upward motion of the plunger device 40 within the housing. The alignment hole 39 and slot 36 are designed to slidably receive a plunger device 40 and prevent racking of the plunger device 40 during operation.

The two wiper arms 24 are pivotally connected to the transmission bracket 30. Furthermore, each of the wiper arm 24 gear teeth 27 mesh with the plunger device 40 gear teeth. In at least one example, the gear teeth on gear rack 42 on the plunger device 40 mesh with their respective wiper arm pivot gear 26 gear teeth 27. Finally, each wiper blade element 21 is configured to touch at least one lens 4.

In at least one embodiment of the housing, the transmission bracket cover 50 is secured to the transmission bracket 30, forming a waterproof seal around the components within the transmission bracket 30. In yet other examples, the longitudinal stop surface 54 may be configured to impede the top of the vertical stop post 46. By impeding the vertical stop post 46, the plunger device 40, extends only partially into the transmission bracket 30. This maintains some compression in the biasing element 48 between the transmission bracket 30 and the plunger device 40. This compression improves the comfort and feel for a user depressing the plunger 40.

Figure 4B:
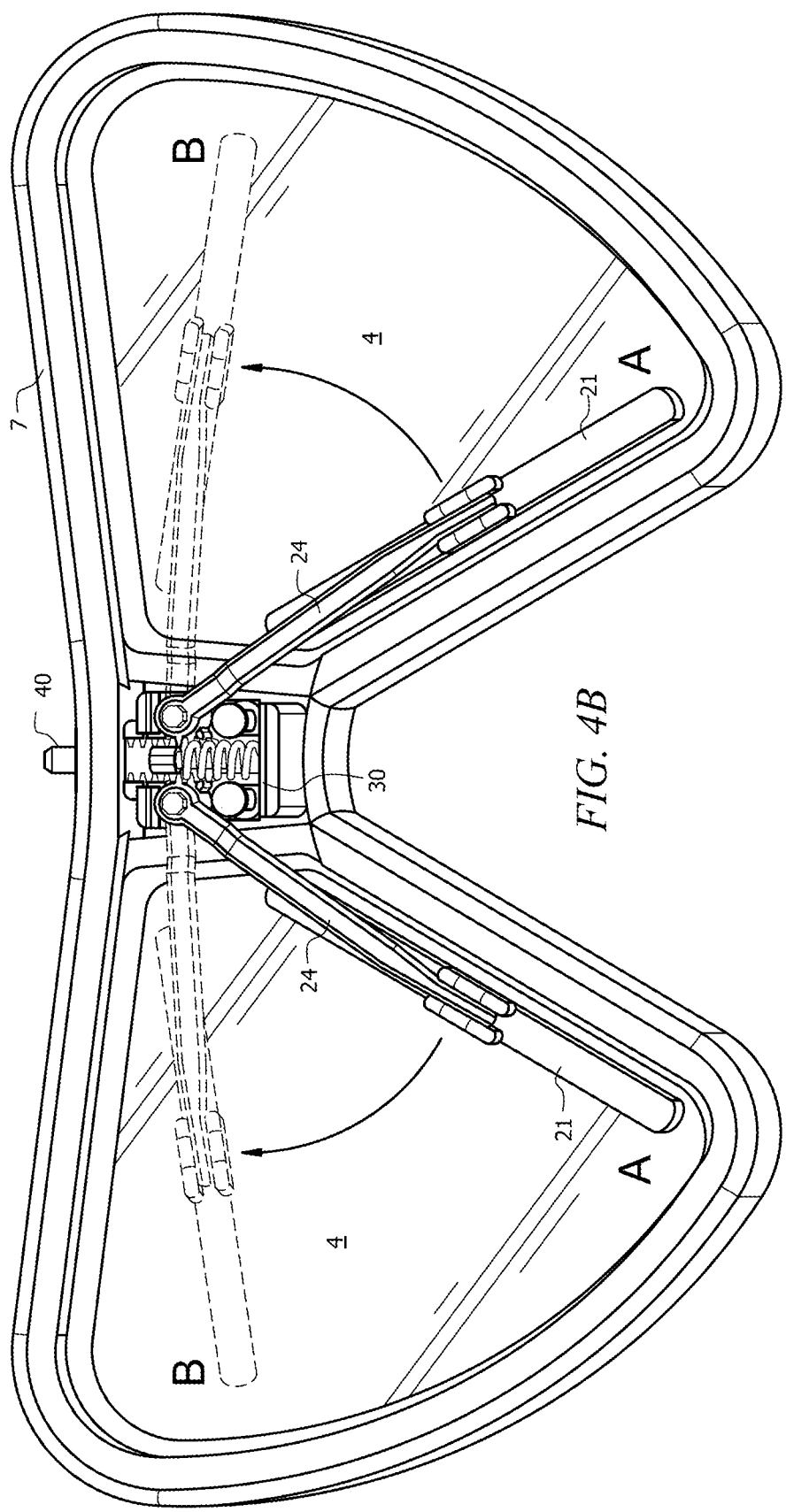
Figure 5:
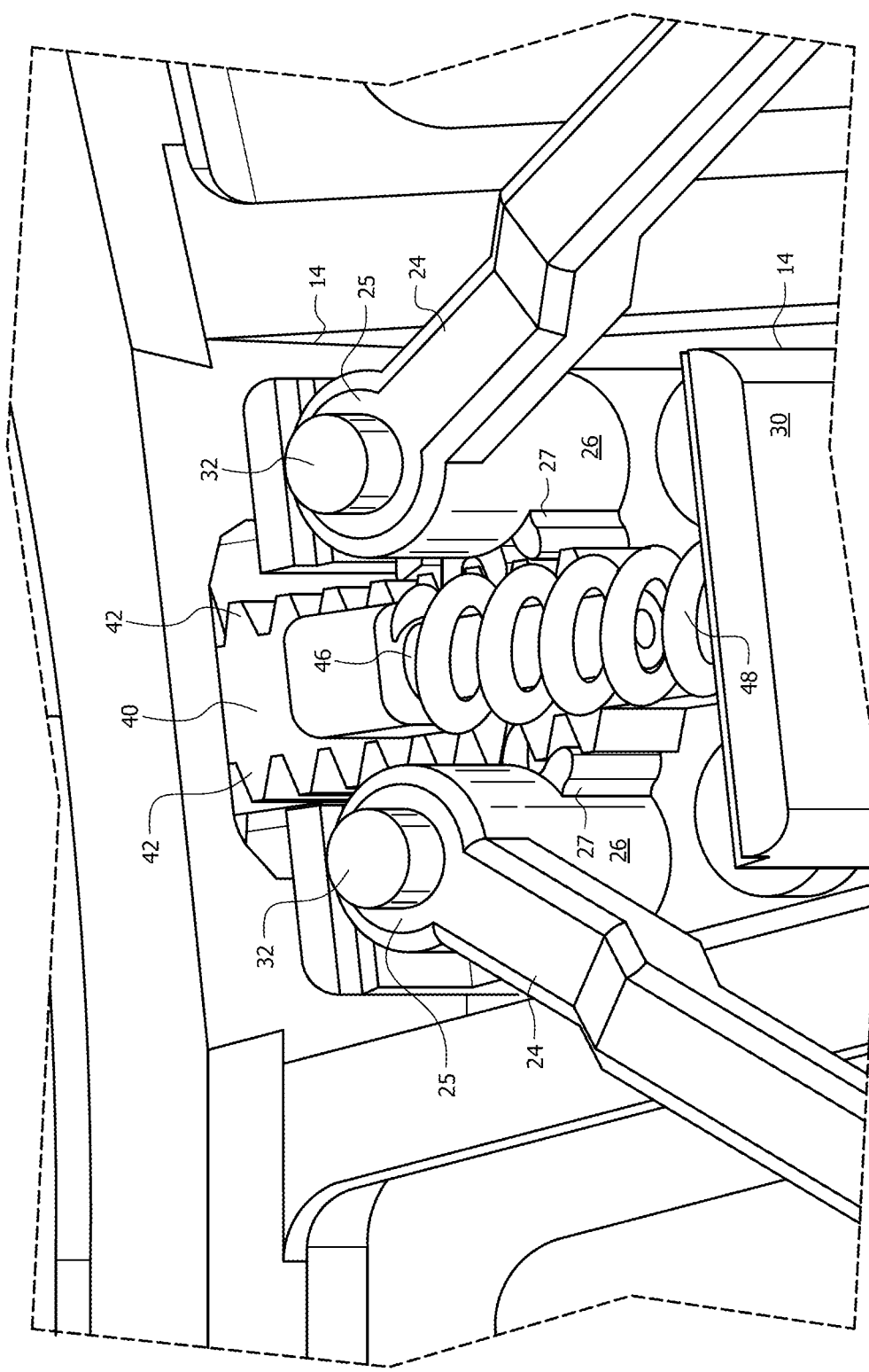

FIGS. 4B and 5 illustrate how the wiper mechanism 20 clears condensation when activated by a user. In a first or resting position A, the plunger device 40 extends to its maximum extent out of the top of the transmission bracket 30. The gear teeth on each of the vertical gear racks 42 are enmeshed with the respective gear teeth 27 on a wiper arm pivot gear 26. When the user depresses the plunger device 40 the enmeshed gear teeth cause the two wiper arm pivot gears 26 to pivot about the upper aligner post and pivot points 32, which in turn causes the two wiper arms 24 to pivot in an upward motion. Depressing the plunger device 40 also causes the biasing element 48 to compress storing potential energy in the biasing element 48. Because each wiper arm 24 pivots, the wiper blade element 21 positioned at the second or distal end 28 of each wiper arm 24 also pivots. The pivoting of each wiper blade element 21 moves each wiper blade element 21 across the at least one lens 4 to a second or extended position B, clearing condensation by brushing the condensation away from the at least one lens 4. When the user releases the plunger device 40 the biasing element 48 rebounds due to its stored potential energy, extending the plunger device 40 outward from the transmission bracket 30. By extending the plunger device 40, the enmeshed gear teeth on the vertical gear racks 42 and the wiper arm pivot gears 26 cause the two wiper arms 24 to pivot back to the first or resting position A. The pivoting of each of the wiper arms 24 again moves each wiper blade element 21 across the at least one lens 4 back to the first or resting position A, clearing any remaining condensation by brushing the condensation away from the at least one lens 4.

An illustration of an example of how the wiper mechanism 20 can be implemented into a frame 7 can be more clearly seen in FIG. 5. The plunger device 40 is slidably coupled to the transmission bracket 30, which is affixed into the recess 14 formed in the frame 7. The gear teeth of the opposing vertical gear racks 42 of the plunger device 40 mesh with the gear teeth 27 on each respective wiper arm pivot gear 26. The two wiper arms 24 are pivotally connected to the two upper aligner post 32, which perpendicularly extend from the vertical wall 35 of the transmission bracket 30. The biasing element 48 is positioned about the vertical stop post 46 and touching the bottom surface 37 of the transmission bracket 30.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

It will now be evident to those skilled in the art that there has been described herein an improved wiper mechanism for interior lens surfaces of various vision protective devices. Although the invention hereof has been described by way of a preferred embodiment, it will be evident that other adaptations and modifications can be employed without departing from the spirit and scope thereof. For example, the wiper mechanism could easily be adapted to ski goggles or a protective face shield used in laboratories and other industrial settings. The terms and expressions employed herein have been used as terms of description and not of limitation; and thus, there is no intent of excluding equivalents, but on the contrary it is intended to cover any and all equivalents that may be employed without departing from the spirit and scope of the invention.

I claim:
1. A wiper mechanism, comprising:
   a transmission housing comprising
      a transmission bracket having a vertical wall, a first opposing surface and a second opposing surface connected to the vertical wall, wherein a biasing element is positioned between a plunger device and a vertical stop post and the first opposing surface;

two upper aligner posts perpendicularly extending from the vertical wall;
an alignment hole in the second opposing surface, wherein the plunger device extends outward from the alignment hole; and;
the plunger device coupled to the transmission housing, said plunger device comprising gear teeth configured on opposing vertical gear racks and a vertical stop post;
the biasing element positioned between the transmission housing and the plunger device;
two wiper arms pivotally connected to the transmission housing, each wiper arm comprising:
a pivot gear positioned at a first end of the wiper arm, said pivot gear comprising gear teeth and a pivot point aperture pivotally connected to one of the two upper aligned posts,
a wiper blade element positioned at a second end of the wiper arm;
wherein the gear teeth of each wiper arm pivot gear are enmeshed with the plunger device gear teeth so that the two wiper arms pivot when the plunger device is depressed.

2. The wiper mechanism of claim 1 further comprising:
a mask having:
at least one lens;
a frame securing the at least one lens and the wiper mechanism, wherein the wiper mechanism is set within the frame so that each wiper arm wiper blade element contacts the at least one lens; and
a head strap.

3. The wiper mechanism of claim 2, wherein the mask further comprises a face-fitting skirt peripherally extending from the frame to the face of a user, when worn.

4. The wiper mechanism of claim 3, wherein the face-fitting skirt forms a water-excluding seal with the face of the user, when worn.

5. The wiper mechanism of claim 2, further comprising a waterproof seal between the plunger device and the frame of the mask.

6. The wiper mechanism of claim 5, wherein said waterproof seal comprises an o-ring configured about the plunger device.

7. The wiper mechanism of claim 5, wherein said waterproof seal comprises a waterproof cover between the plunger device and the frame of the mask.

8. The wiper mechanism of claim 1, wherein:
the transmission housing further comprises a transmission bracket cover, wherein the transmission bracket cover secures the two wiper arms to the upper aligner posts; and
means for securing the transmission bracket cover to the transmission bracket.

9. The wiper mechanism of claim 8, wherein each wiper blade element is pivotally connected to the second end of its respective wiper arm.

10. A method of manufacturing a wiper mechanism, the method comprising:
providing a transmission housing, wherein the transmission housing further comprises:
a transmission bracket having a vertical wall, first and second opposing surfaces connected to the vertical wall, wherein a biasing element is positioned between a plunger device and a vertical stop post and the first opposing surface;
two upper aligner posts perpendicularly extending from the vertical wall;
an alignment hole in the second opposing surface, wherein the plunger device extends outward from the alignment hole; and
forming the plunger device comprising gear teeth for coupling to the transmission housing, wherein the plunger device further comprises:
opposing vertical gear racks comprising the gear teeth, and
a vertical stop post;
forming two wiper arms for pivotally connecting to the transmission housing, wherein each wiper arm comprises a pivot gear positioned at a first end of the wiper arm and comprising gear teeth, and a wiper blade element positioned at a second end of the wiper arm, wherein each wiper arm pivot gear further comprises a wiper arm pivot point aperture, wherein each wiper arm pivot point aperture is pivotally connected to one of the upper aligner posts; and
providing the biasing element for positioning between the transmission housing and the plunger device.

11. The method of claim 10, further comprising;
coupling the plunger device to the transmission housing;
connecting the two wiper arms to the transmission housing;
positioning the biasing element between the transmission housing and the plunger device; and
meshing each wiper arm pivot gear teeth set with the plunger device gear teeth, wherein each wiper arm pivot gear teeth set meshes with the plunger device gear teeth such that the two wiper arms pivot when the plunger device is depressed.

12. The method of claim 11, further comprising:
forming a mask, comprising:
at least one lens;
a frame for securing the at least one lens and the wiper mechanism;
a head strap; and
securing the at least one lens and the wiper mechanism to the frame, wherein the wiper mechanism is set within the frame so that each wiper arm wiper blade element contacts the at least one lens.

13. The method of claim 12, wherein the mask further comprises a face-fitting skirt peripherally extending from the frame to the face of a user.

14. The method of claim 13, wherein the face-fitting skirt forms a water-excluding seal with the face of the user.

15. The method of claim 12, further comprising:
coupling the plunger device to the transmission housing:
connecting the two wiper arms to the transmission housing, wherein the two wiper arms are pivotally connected to the upper aligner posts;
positioning the biasing element between the transmission housing and the plunger device;
meshing each wiper arm pivot gear teeth set with the plunger device gear teeth, wherein each wiper arm pivot gear teeth set is enmeshed with the plunger device gear teeth so that the two wiper arms pivot when a user depresses the plunger device.

16. The method of claim 12, further comprising:
forming a transmission bracket cover for securing each of the two wiper arms onto its respective upper aligner post and pivot point; and
providing means for securing the transmission bracket cover to the transmission bracket.

17. The method of claim 12, further comprising providing a waterproof seal between the plunger device and the frame of the mask.

18. A vision protection apparatus, comprising:
at least one lens;
a frame securing the at least one lens;
means for attaching the frame to the head of a user;
a wiper mechanism, comprising:
- a transmission housing, comprising an alignment hole;
- a plunger device comprising gear teeth, wherein the plunger device is fitted in the alignment hole so that the plunger device slides within the transmission housing;
- a biasing element positioned between the transmission housing and the plunger device;

two wiper arms pivotally connected to the transmission housing, each wiper arm comprising:
- a pivot gear positioned at a first end of the wiper arm, said pivot gear comprising gear teeth,
- a wiper blade element positioned at a second end of the wiper arm;
- wherein the gear teeth of each wiper arm pivot gear are enmeshed with the plunger device gear teeth so that the two wiper arms pivot when the plunger device is depressed.

19. The vision protection apparatus of claim 18, further comprising a face-fitting skirt peripherally extending from the frame to the face of the user, when worn.

20. The vision protection apparatus of claim 19, wherein the face-fitting skirt forms a water-excluding seal with the face of the user, when worn.

\* \* \* \* \*